United States Patent [19]

Kane et al.

[11] Patent Number: 5,339,153
[45] Date of Patent: Aug. 16, 1994

[54] LABEL INSPECTION MACHINE

[75] Inventors: William J. Kane, Geneva; Gregory A. Chouinard, Wasco, both of Ill.

[73] Assignee: The Label Printers, Aurora, Ill.

[21] Appl. No.: 985,021

[22] Filed: Dec. 3, 1992

[51] Int. Cl.5 ............................................ G01N 21/89
[52] U.S. Cl. ................................... 356/394; 356/430; 250/562; 250/572
[58] Field of Search ............... 356/394, 429, 430, 431, 356/237; 350/561, 562, 563, 572

[56] References Cited

U.S. PATENT DOCUMENTS

| 4,644,341 | 2/1987 | Warner. | |
| 5,058,175 | 10/1991 | Aso | 356/394 |
| 5,187,376 | 2/1993 | Hashimoto et al. | 250/572 |

FOREIGN PATENT DOCUMENTS 85144  5/1983  Japan .................................... 356/237

*Primary Examiner*—F. L. Evans
*Attorney, Agent, or Firm*—Wood, Phillips, VanSanten, Hoffman and Ertel

[57] ABSTRACT

A label inspection system automatically inspects print on labels carried seriatim on a web. The system comprises a photoelectric sensing system including a light inspection sensor sensing reflected light and an electrical control circuit providing an output at a select first or second electrical state dependent upon sensed reflected light being above or below a select level. The sensor is mounted at a select transverse position in a path of movement of the web to sense reflected light along a select longitudinal path of the web, the select longitudinal path including a portion of the labels carried on the web intended to have print, the print acting to minimize reflected light. A detect sensor sense proximity of the inspection sensor relative to a select longitudinal portion of each successive label and provide an enable signal relative thereto. A control circuit is operatively coupled to the sensing system and the detect sensor including a logic circuit for analyzing the sensing system output only when the enable signal is received, and an output circuit for indicating the presence or absence of print on each label dependent upon if reflected light is above or below the select level when the logic circuit is analyzing the sensing system output.

15 Claims, 4 Drawing Sheets

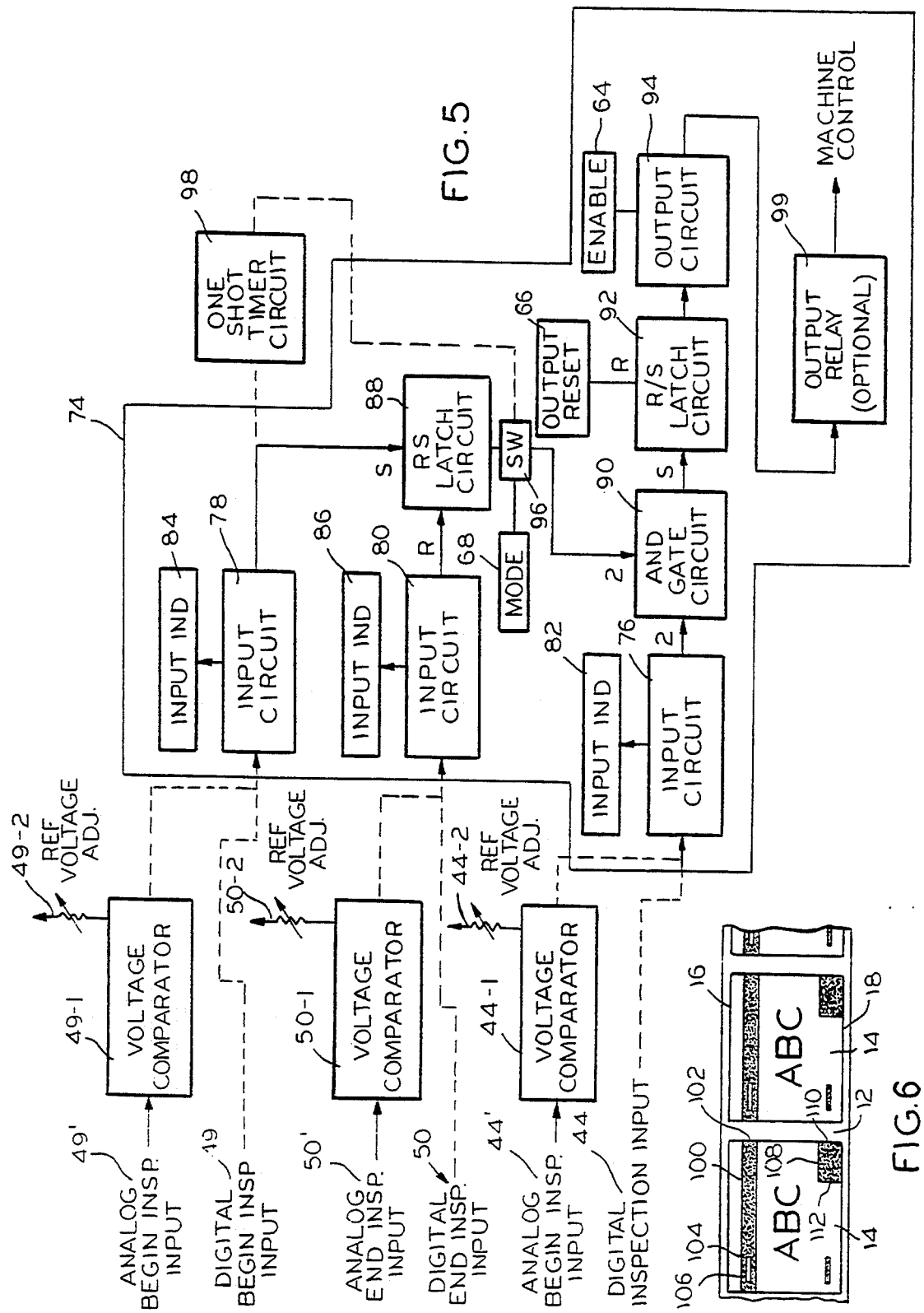

LABEL INSPECTION MACHINE

FIELD OF THE INVENTION

This invention relates to a label inspection machine and, more particularly, an inspection machine that inspects labels separate from the printing press.

BACKGROUND OF THE INVENTION

A typical product label is made of a paper or other similar substrate having printing inks printed thereon according to the product with which the label is to be used. Typically, the labels are carried seriatim on a web using a resealable adhesive so that the labels can be removed from the web and adhered to a product or packaging for the product.

With certain labels, such as for pharmaceutical products, strict requirements must be adhered to as to the proper printing on the label. For example, with such pharmaceutical products the Food and Drug Administration mandates that full printing be included on the label. A typical label includes printing in at least one ink color on the label substrate. Therefore, there is a need for monitoring the absence of the color or copy on the substrate.

Known systems have taken photographic images of the label with the image being digitized and compared to a stored reference image. Such a system is rather complex and expensive. Other systems print a solid box in the waste area of the label and check to see if the box is missing. This is done on the printing press itself. This presents a problem in that when the press stops due to a sensed printing error, a stop mark is produced in the printing which creates a second bad area.

The present invention is intended to overcome one or more of the problems discussed above in a novel and simple manner.

SUMMARY OF THE INVENTION

In accordance with the invention there is disclosed a label inspection system which inspects for missing or faded color or copy on the label.

Broadly, there is disclosed herein a label inspection system for automatically inspecting print on labels carried seriatim on a web. The system comprises a photoelectric sensing system including a light sensor sensing reflected light and an electrical control circuit providing an output at a select first or second electrical state dependent upon sensed reflected light being above or below a select level. Means mount the sensor at a select transverse position in a path of movement of the web to sense reflected light along a select longitudinal path of the web, the select longitudinal path including a portion of the labels carried on the web intended to have print, the print acting to minimize reflected light. Detect means sense proximity of the sensor relative to a select longitudinal portion of each successive label and provide an enable signal relative thereto. A control circuit is operatively coupled to the sensing system and the detect means including logic means for analyzing the sensing system output only when the enable signal is received, and an output circuit for indicating the presence or absence of print on each label dependent upon if reflected light is above or below the select level when the logic means is analyzing the sensing system output.

In accordance with one aspect of the invention, the sensing system comprises an analog sensor developing an analog voltage signal proportional to reflected sensed light, a reference circuit developing a select reference voltage, and a voltage comparator comparing the analog voltage signal to the reference voltage.

It is a feature of the invention that the detect means comprises a proximity sensor sensing proximity of a select longitudinal portion of a web related to position of the portions of the label having print thereon relative to the light sensor, and a timer providing the enable signal for a select time duration after the proximity sensor senses the select longitudinal portion of the web.

It is another feature of the invention that the detect means comprises first and second longitudinally spaced proximity sensors, each sensing proximity of a select longitudinal position of a web respectively related to leading and trailing positions of the portions of the label having print thereon relative to the light sensor, and a latch circuit providing the enable signal between the times at which the select longitudinal position is sensed by the first and second proximity sensors.

It is a feature of the invention that the logic circuit comprises a logic AND gate.

It is another feature of the invention that the output circuit comprises an output control relay.

It is a further feature of the invention that the mounting means comprises a frame overlying the path of movement of a web, the frame defining a plurality of select transverse and longitudinal mounting positions of the sensor.

In accordance with another aspect of the invention, the label inspection system includes a plurality of photoelectric sensing systems.

It is an additional feature of the invention that the mounting means comprises a frame overlying a path of movement of a web, the frame defining a plurality of select transverse and longitudinal mounting positions of the light sensor.

It is a further feature of the invention wherein a plurality of control circuits are provided and further comprising a plurality of select means for selectively connecting each sensing system to one of the control circuits.

Further features and advantages of the invention will be readily apparent from the specification and from the drawing.

BRIEF DESCRIPTION OF THE DRAWING

FIG. 5 is a block diagram of a control circuit for a label inspection system according to an alternative embodiment of the invention; and FIG. 6 is a plan elevation view of a web carrying a plurality of labels.

DETAILED DESCRIPTION OF THE DRAWING

Figure 1:
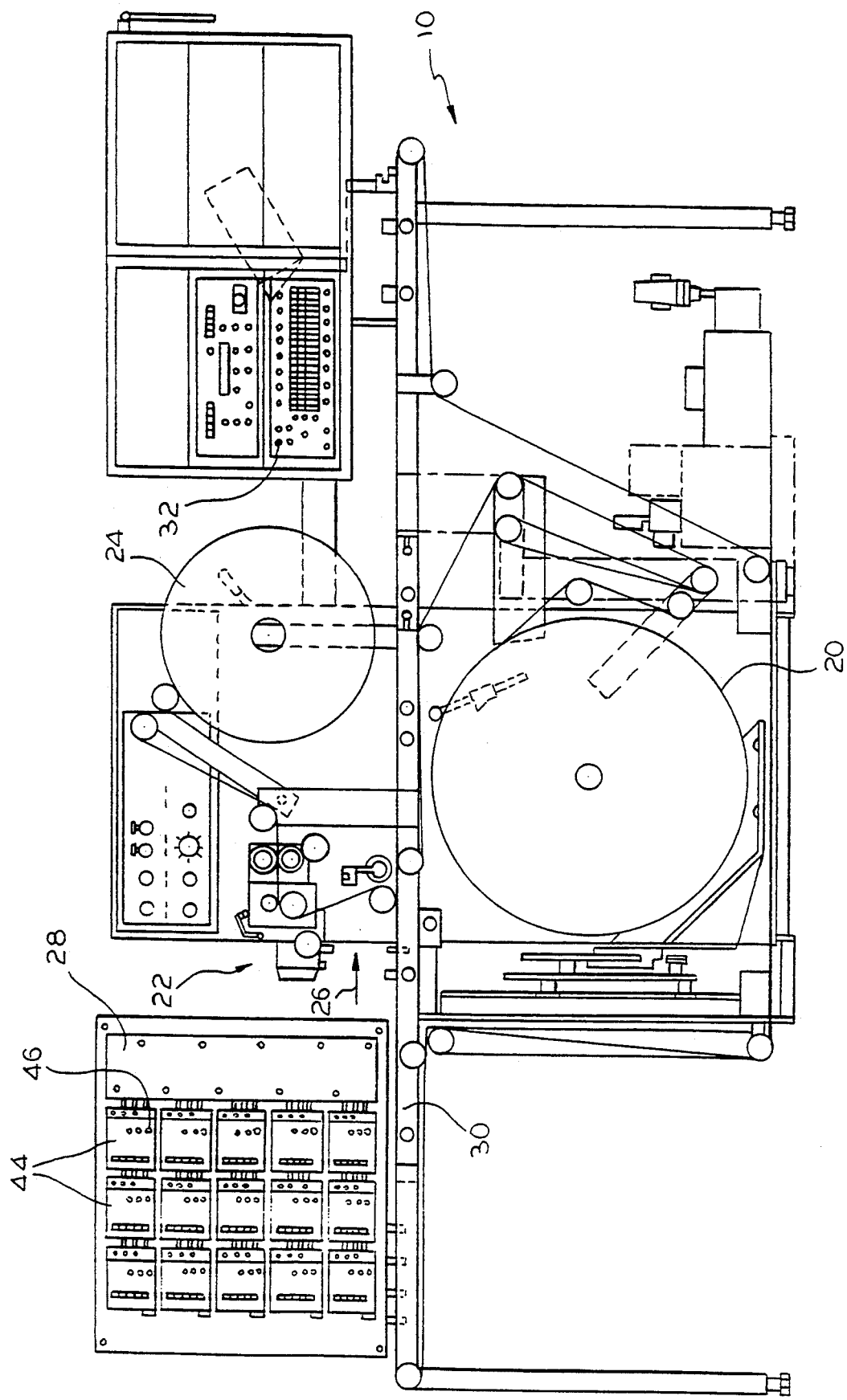
FIG. 1 is a front elevation view of a label cutting and roll machine including the label inspection system according to the invention.

With reference to FIG. 1, a label cutting and roll machine 10 is illustrated including a label inspection system according to the invention.

With reference also to FIG. 6, the machine 10 is used in connection with a web 12 carrying a plurality of labels 14 carried seriatim thereon. Each label 14 is included with printed copy thereon. The copy is provided by applying printing ink to the label at a printing press. Each label 14 is longitudinally spaced on the web 12. The labels 14 are printed as by passing under a print cylinder (not shown) with an outer cylinder surface printing in a transverse line on each label 14 as the web 12 moves longitudinally. Particularly, the print area which will engage a print cylinder at any given time is across the label 14 between side edges 16 and 18. Thus, if an error in printing occurs, the error will likely occur across the entire width of the label. In accordance with the invention, a select longitudinal portion of the label 14 is inspected to sense error in printing.

In FIG. 6, the labels are shown carried in one row on the web 12. Often, for printing efficiencies, the web 12 will be much wider and carry multiple rows of labels 14. The label cutting and roll machine of FIG. 10 carries such a printing web on a roll 20, with the web being carried to a cutting station 22 and then stored on a roll 24 in a single width configuration, as shown in FIG. 6. Particularly, the web moves from left to right entering the cutting area 22, as illustrated by the arrow 26. Particularly, the web moves past the label inspection input station 28 as they move across a conveying system 30 from the input roll 20 to the die cutting station 22. A control panel 32 provides operator input and output functions for controlling the label inspection system.

Figure 2:
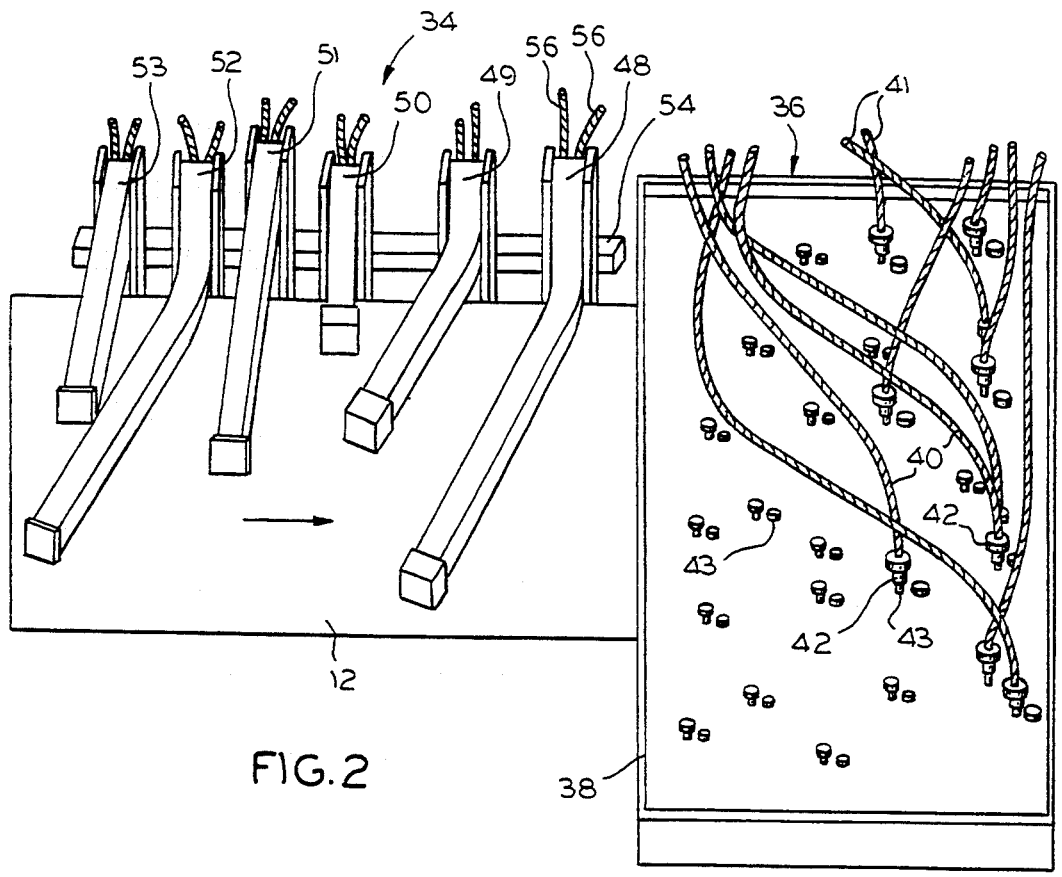
FIG. 2 is a perspective view of a portion of the machine of FIG. 1 particularly illustrating the sensing devices for the label inspection system.

With reference to FIG. 2, a web 12 is illustrated schematically moving from left to right relative to a detect system 34 and an inspection system 36 forming part of the label inspection system.

The sensing system 36 comprises a locating plate or frame 38 overlying a path of movement of the web 12. The frame 38 supports a plurality of inspection sensors 40 at select transverse and longitudinal mounting positions of the frame 38. As used herein, the term "longitudinal mounting positions" refers to position in a direction corresponding to movement of the web 12, while "transverse position" relates to position across the web 12. Particularly, each inspection sensor 40 is at a position corresponding to an area in which print on a label 14 is to be sensed.

Each inspection sensor 40 comprises a fiber optic cable 41 having a sensing end 42 inserted into one of a plurality of openings 43 in the frame 38 and an opposite end coupled to a control panel 44, see FIG. 1. Each inspection sensor 40 may be in accordance with the photoelectric sensing system described in Warner, U.S. Pat. No. 4,644,341, the specification of which is hereby incorporated by reference herein. Such a system includes a light transmitting lens and receiving lens in the control panel 44 for transmitting light and receiving reflected light via the fiber optic cable 41 to the sensing end 42. A select amount of light is transmitted through the cable 41 where it is directed through the opening 43. Light reflected back to the sensing end is returned to the control panel 44. The amount of sensed reflected light is compared to a reference value selected by controlling position of a control knob 46 for selecting a desired reference value. The reference value will be selected according to the color of ink printed on the label as the amount of light reflected depends upon the printing density and color of the particular ink used.

The detect system 34 comprises a plurality of movable through beam sensors 48-53. Particularly, each sensor 48-53 is movably positioned on a crossbar 54 to be mounted at a select longitudinal position relative to the frame 38. Each sensor 48-53 is similar to the sensing system 40 discussed above, except that two fiber optic cables 56 are used, one on either side of the web 12, connected to the two lenses. This is illustrated schematically in FIG. 4. Particularly, the transmitter transmits light which is received by the receiver as controlled by one of the control panels 44, see FIG. 1. Each such detecting system may also be as described in U.S. Pat. No. 4,644,341 incorporated by reference herein.

The web 12 is often made of a translucent material which permits light to pass therethrough. Thus, as the web 12 passes through each sensor 48-53, the light is transmitted through the web to the receiver when a portion of the web between labels 14 is across the beam, while the presence of a label 14 will block the beam to stop transmission of light. The threshold amount of light to be detected is controlled using one of the control knobs 46, as discussed above.

In the illustrated embodiment, two of the sensors 48-53 of the detect system 34 are used with one of the inspection sensors 40. The two sensors, such as the detectors 49 and 50, detect a select leading or trailing edge of a label 14 which correspond to a select leading or trailing portion of an area of the label 14 to be inspected being present at the sensing system 36. For example, the position of each sensor 48-53 is selected relative to that of the corresponding cable end 42 to provide synchronization of signals to be used. This allows the label inspection system to look at a select portion of the label and not other portions, or to look at a select point of a label to a second point of the label. In accordance with the invention, the system is operable to sense a plurality of distinct areas on each label 14 or to concurrently inspect multiple labels simultaneously using a multiple channel configuration. In the illustrated embodiment of the invention, four channels are provided for sensing four distinct print areas on each label or a plurality of labels mounted transversely on a web 12. Also, the system illustrated is described in connection with a system including up to twelve fiber optic inspection sensors 40.

Figure 3:
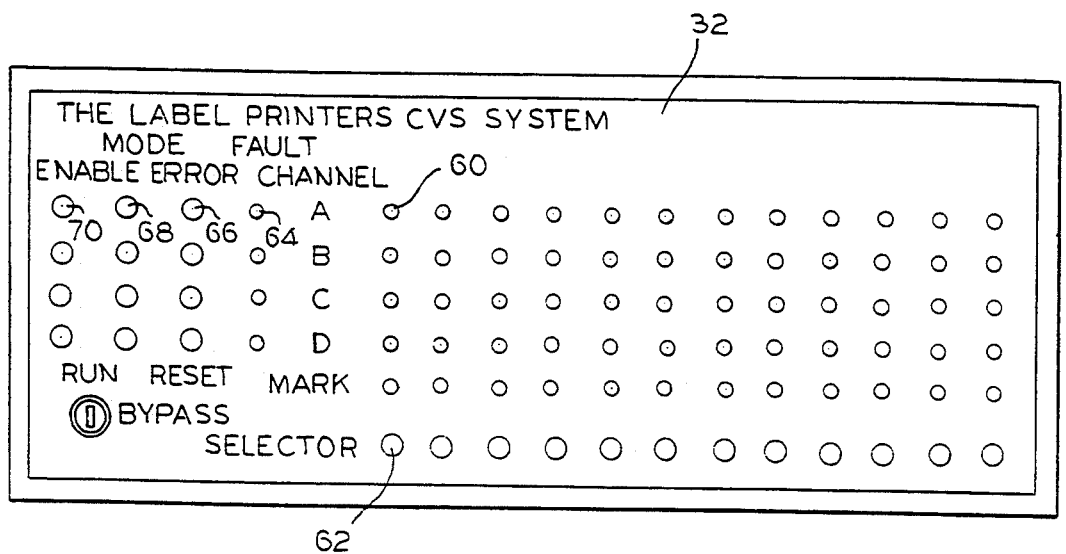
FIG. 3 is a front elevation view of a control panel for the label inspection system.

With reference to FIG. 3, the control panel 32 includes twelve columns of LED's 60, one for each inspection sensing system 40. Each column has four LED's, one for each of the four channels labeled "A", "B", "C" and "D", as well as a fifth LED, labeled "Mark" and a selector knob 62. The selector knob 62 is rotated to operatively connect each of the fiber optic inspection sensing systems 40 to one of the channels. The panel 32 also includes a FAULT LED 64 for each channel, an ERROR RESET illuminated button 66 for each channel, a MODE SELECT illuminated button 68 for each channel and an ENABLE illuminated button 70 for each channel.

Figure 4:
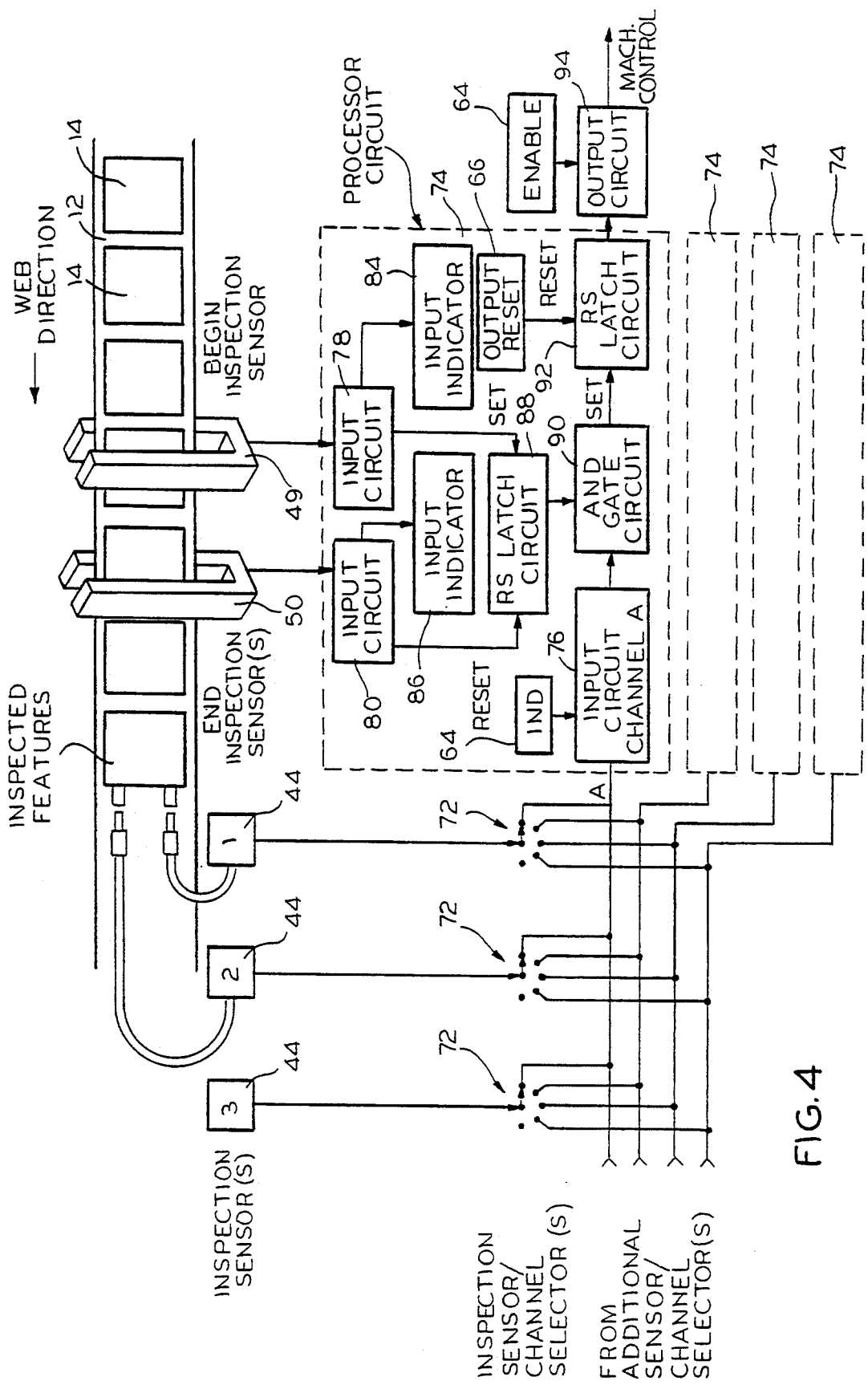
FIG. 4 is a generalized illustration and block diagram for the label inspection system according to the invention.

With reference to FIG. 4, the label inspection system is illustrated in greater detail. Each of the inspection sensor control panels 44 is connected to a five position selector switch 72, one for each knob 62. Each switch 72 includes four outputs, one for each channel. A processor circuit 74 is provided for each channel, only one of which is illustrated in detail. The processor circuit 74 is illustrated for channel A and includes an input circuit 76 connected to one output of each of the switches 72. Similar input circuits 78 and 80 are provided connected to the detect inspection sensors 49 and 50, respectively. The input circuits 76, 78 and 80 include inverter circuits for converting a low sinking input to a high logic signal. The input circuit 76 is connected to the associated channel fault LED 64 of the control panel 32. The input circuits 78 and 80 are connected to respective input indicators 84 and 86, inside the control panel 32. The input circuits 78 and 80 are respectively connected to the SET and RESET inputs of an RS latch circuit 88. Particularly, the first input circuit 78 comprises a BEGIN INSPECTION sensor which senses a select edge of one of the labels 14 corresponding to a leading edge of the printing area to be inspected being proximate the inspection sensor 44 being used. The sensor 50 comprises an END INSPECTION sensor sensing a trailing edge of one of the labels 14 corresponding to a trailing edge of the portion of the label being inspected being proximate the particular inspection sensor 44. Thus, the RS latch circuit provides a latched output to an AND gate circuit 90 only during the time at which the select longitudinal portion of each successive label is proximate the inspection sensor 44 and the signal to the AND gate 90 comprises an ENABLE signal. Another input of the AND gate circuit is connected to the input circuit 76. An output of the AND gate circuit 90 is connected to the SET input of an RS latch circuit 92 whose reset input is connected to the ERROR RESET button 66, see FIG. 3. As a result, the AND gate is operated when enabled, i.e., when light is to be detected as determined by the latch circuit 88 as by analyzing the status of the input circuits 76 to determine if its output is high, indicating the absence of print or copy on a label 14 currently being inspected. When such conditions exist, then the output of the RS latch circuit 92 is latched to provide a controlling output to an output circuit 94 connected to a machine control for shutting down the machine based on the detection of an error in printing. The output circuit 94 is thus controlled to indicate the presence or absence of print on each label 14 dependent upon if reflected light is above or below the select level when the AND gate 90 is analyzing the sensing system input circuit 76.

With reference to FIG. 6, the system can be used to sense printed ink in area of the label 14. For example, the elongate print area 100 can be sensed starting at a leading edge 102 and ending at a trailing edge, such as 104, prior to an area at which less printing is provided, such as the name of the manufacturer being included at 106. Alternatively, a printing block 108 can be sensed between a leading edge 110 and a trailing edge 112. Each inspection sensor 40 senses an area 1/16 inch in diameter. In addition to sensing the portions 100 and 108 on FIG. 6, it can be used for a spot look to examine a particular spot on the label such as a portion of one of the letters A, B or C, see FIG. 6.

In use, the leading edge of an area to be detected is positioned below the sensing end 42 of the inspection sensor 40 being used. The knob 62 for such sensor 42 is set to channel A, causing the A channel LED 60 for that sensor to be illuminated. The begin inspection sensor 49 is positioned to sense a leading edge of another label 14. A similar procedure is used for positioning the end inspection sensor 50.

As the web 12 moves relative the inspection system, the fault LED 64 is illuminated when the inspection sensor senses an undesirable condition, i.e., missing or faded ink. However, this signal is analyzed only when the AND gate 90 is enabled by the RS latch circuit. If printed copy is missing or faded at a desired position, then the output latch circuit 92 is latched, illuminating the error light of the button 66, This circuit 92 is reset by depressing the button 66.

With reference to FIG. 5, a block diagram illustrates an alternative embodiment of the invention including a processor circuit 74 similar to that described above. The processor circuit differs, in part, in the use of the mode switch 68 for operating a switch 96 between the output of the RS latch circuit 88 and the AND gate circuit 90. Another input of the switch 96 is connected to a one shot timer circuit 98 having its input connected to the input circuit 78. This feature is used in connection with a spot look feature in which upon actuating the mode button 68, the AND gate circuit 90 is connected to the one shot timer circuit 98 instead of the RS latch circuit 88. In this embodiment, when the input circuit 78 goes high, sensing the leading edge of a label 14 corresponding to a particular point on another label being present in proximity to an inspection sensor 44, the one shot timer circuit provides an output for a select time duration to the AND gate circuit 90. Thus, the AND gate circuit 90 is enabled for a select time duration, on the order of 10-15 milliseconds, rather than based on a duration corresponding to a print area on the label. The time duration is generally relatively short to detect ink on a particular spot, such as a portion of one of the letters on the label 14, see FIG. 6. This circuit also shows an optional output relay 99 interposed between the output circuit 94 and the machine control for controlling the same.

The inspection sensors 40 and the detect inspection sensors 49 and 50 are digital inasmuch as they produce a logic high or low signal according to the amount of light detected. Alternatively, analog sensors 49', 50' and 44' of conventional construction could be included connected to voltage comparators 49-1, 49-2 and 44-3, respectively, each also connected to a reference voltage adjustment circuit 49-2, 50-2, and 44-2. The output of each voltage comparator 49-1, 50-1 and 44-1 is connected to the respective input circuit 78, 80 and 76. In all other respects, the system operated in a similar manner as described above.

Thus, in accordance with the invention, there is illustrated a label inspection system which inspects presence or absence of print or copy on select portions of a labels off press. The system inspects actual copy, rather than waste area. The inspection sensors 44 operate off fiber optic cables 41 which, in accordance with the control circuit 74, look at a select portion of the label comprising a longitudinal area portion or a particular spot on the label.

The embodiment of the invention described herein is illustrative of the broad inventive concepts comprehended by the invention.

We claim:

1. A label inspection system for automatically inspecting print on labels carried seriatim on a web, comprising:

a photoelectric sensing system including a light sensor sensing reflected light and an electrical control circuit providing an output at a select first or second electrical state dependent upon sensed reflected light being above or below a select level;

means mounting said sensor at a select transverse position in a path of movement of the web to sense reflected light along a select longitudinal path of the web, said select longitudinal path including a portion of the labels carried on the web intended to have print, said print acting to minimize reflected light;

detect means for sensing proximity of said sensor relative to a select longitudinal portion of each successive label and providing an enable signal relative thereto; and a control circuit operably coupled to said sensing system and said detect means including logic means for analyzing said sensing system output only when said enable signal is received, and an output circuit for indicating the presence or absence of print on each label dependent upon if reflected light is above or below the select level when said logic means is analyzing said sensing system output.

2. The label inspection system of claim 1 wherein said sensing system comprises an analog sensor developing an analog voltage signal proportional to reflected sensed light, a reference circuit developing a select reference voltage, and a voltage comparator comparing said analog voltage signal to said reference voltage.

3. The label inspection system of claim 1 wherein said detect means comprises a proximity sensor sensing proximity of a select longitudinal portion of a web related to position of the portions of the label having print thereon relative to said light sensor and a timer providing said enable signal for a select time duration after said proximity sensor senses the select longitudinal portion of the web.

4. The label inspection system of claim 1 wherein said detect means comprises first and second longitudinally spaced proximity sensors each sensing proximity of a select longitudinal position of a web respectively related to leading and trailing positions of the portions of the label having print thereon relative to said light sensor and a latch circuit providing said enable signal between the times at which the select longitudinal position is sensed by said first and second proximity sensors.

5. The label inspection system of claim 1 wherein said logic means comprises a logic AND gate.

6. The label inspection system of claim 1 wherein said output circuit comprises an output control relay.

7. The label inspection system of claim 1 wherein said mounting means comprises a frame overlying a path of movement of a web, said frame defining a plurality of select transverse and longitudinal mounting positions of said light sensor.

8. A label inspection system for automatically inspecting plural print areas on labels carried seriatim on a web, comprising:

a plurality of photoelectric sensing systems each including a light sensor sensing reflected light and an electrical control circuit providing an output at a select first or second electrical state dependent upon sensed reflected light being above or below a select level;

means mounting each said sensor at select transverse positions in a path of movement of the web to sense reflected light along select longitudinal paths of the web, each said select longitudinal path including a portion of the labels carried on the web intended to have print, said print acting to minimize reflected light;

detect means for sensing proximity of each said sensor relative to a select longitudinal portion of each successive label and providing an enable signal relative thereto; and a control circuit operably coupled to each said sensing system and said detect means including logic means for analyzing each said sensing system output only when said enable signal is received, and an output circuit for indicating the presence or absence of print on each label dependent upon if reflected light is above or below the select level when said logic means is analyzing said sensing system output.

9. The label inspection system of claim 8 wherein said sensing system comprises an analog sensor developing an analog voltage signal proportional to reflected sensed light, a reference circuit developing a select reference voltage, and a voltage comparator comparing said analog voltage signal to said reference voltage.

10. The label inspection system of claim 9 wherein said detect means comprises a proximity sensor sensing proximity of a select longitudinal portion of a web related to position of the portions of the label having print thereon relative to said light sensor and a timer providing said enable signal for a select time duration after said proximity sensor senses the select longitudinal portion of the web.

11. The label inspection system of claim 9 wherein said detect means comprises first and second longitudinally spaced proximity sensors each sensing proximity of a select longitudinal position of a web respectively related to leading and trailing positions of the portions of the label having print thereon relative to said light sensor and a latch circuit providing said enable signal between the times at which the select longitudinal position is sensed by said first and second proximity sensors.

12. The label inspection system of claim 9 wherein said logic circuit comprises a logic AND gate.

13. The label inspection system of claim 9 wherein said output means comprises an output control relay.

14. The label inspection system of claim 9 wherein said mounting means comprises a frame overlying a path of movement of a web, said frame defining a plurality of select transverse and longitudinal mounting positions of said light sensor.

15. The label inspection system of claim 8 wherein said system includes one said control circuit for each said sensing system and further comprising a plurality of select means for selectively connecting each said sensing system to one of said control circuits.

* * * * *